United States Patent
Schmidt

(10) Patent No.: US 8,600,482 B2
(45) Date of Patent: Dec. 3, 2013

(54) METHOD AND DEVICE FOR IMAGING A VOLUME SECTION BY WAY OF PET DATA

(75) Inventor: Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 692 days.

(21) Appl. No.: 12/758,925

(22) Filed: Apr. 13, 2010

(65) Prior Publication Data

US 2010/0268063 A1 Oct. 21, 2010

(30) Foreign Application Priority Data

Apr. 15, 2009 (DE) .......................... 10 2009 017 439

(51) Int. Cl.
*G01T 1/161* (2006.01)
*A61B 5/05* (2006.01)

(52) U.S. Cl.
USPC ........................... 600/436; 600/410; 382/128

(58) Field of Classification Search
USPC ................................................. 600/410, 436
See application file for complete search history.

(56) References Cited

U.S. PATENT DOCUMENTS

| | | | |
|---|---|---|---|
| 7,312,455 B2 * | 12/2007 | Manjeshwar et al. | ... 250/363.03 |
| 7,327,138 B2 | 2/2008 | Krieg et al. | |
| 7,465,927 B2 * | 12/2008 | Panin et al. | ............... 250/363.03 |
| 7,683,330 B2 | 3/2010 | Krieg et al. | |
| 2005/0245810 A1 * | 11/2005 | Khamene et al. | ............. 600/410 |
| 2006/0058641 A1 | 3/2006 | Krieg et al. | |
| 2006/0266947 A1 | 11/2006 | Krieg et al. | |
| 2007/0102641 A1 | 5/2007 | Corbeil | |
| 2007/0280556 A1 * | 12/2007 | Mullick et al. | ................ 382/294 |
| 2008/0135769 A1 | 6/2008 | Rosen | |
| 2008/0137930 A1 | 6/2008 | Rosen | |
| 2008/0231275 A1 | 9/2008 | Jattke et al. | |
| 2008/0317194 A1 | 12/2008 | Gagnon et al. | |
| 2009/0037130 A1 | 2/2009 | Feiweier et al. | |
| 2010/0204563 A1 * | 8/2010 | Stodilka et al. | ................ 600/411 |
| 2011/0123083 A1 * | 5/2011 | Ojha et al. | ..................... 382/131 |

FOREIGN PATENT DOCUMENTS

| | | |
|---|---|---|
| DE | 102004043889 | 3/2006 |
| DE | 102005023907 | 12/2006 |
| DE | 102007013564 | 9/2008 |
| DE | 102007034955 A1 | 2/2009 |
| GB | 2449320 | 11/2008 |

OTHER PUBLICATIONS

Steinberg, MRI-based attenuation correction for PET reconstruction, 2008, Ohio State University.*
W. Thomas Dixon, Ph. D.: "Simple Proton Spectroscopic Imaging"; Radiology 1984, 153: p. 189-194; Others; 1984.
Feng Qiao et al.: "Expectation Maximization Reconstruction of PET Image with Non-rigid Motion Compensation", Proceedings of the 2005 IEEE, Engineering in Medicine and Biology 27th Annual Conference Shanghai, China, Sep. 1-4, 2005; Others; 2005.
German Office Action dated May 6, 2009 for priority German patent application No. DE 10 2009 017 439.7-35.

* cited by examiner

*Primary Examiner* — Jacqueline Cheng
(74) *Attorney, Agent, or Firm* — Harness, Dickey & Pierce, P.L.C.

(57) ABSTRACT

A method and a device for imaging a volume section by way of PET data are described. With the proposed solution the PET data of the volume section are acquired by way of a positron emission detector, and the MR data of the volume section are acquired by way of a magnetic resonance system. In at least one embodiment, with the aid of the MR data, PET voxels within the volume section are determined from which radiation occurring due to an annihilation is emitted. The image data are reconstructed from the PET data in that it is taken into account that the PET data are generated only by radiation from the PET voxels.

24 Claims, 2 Drawing Sheets

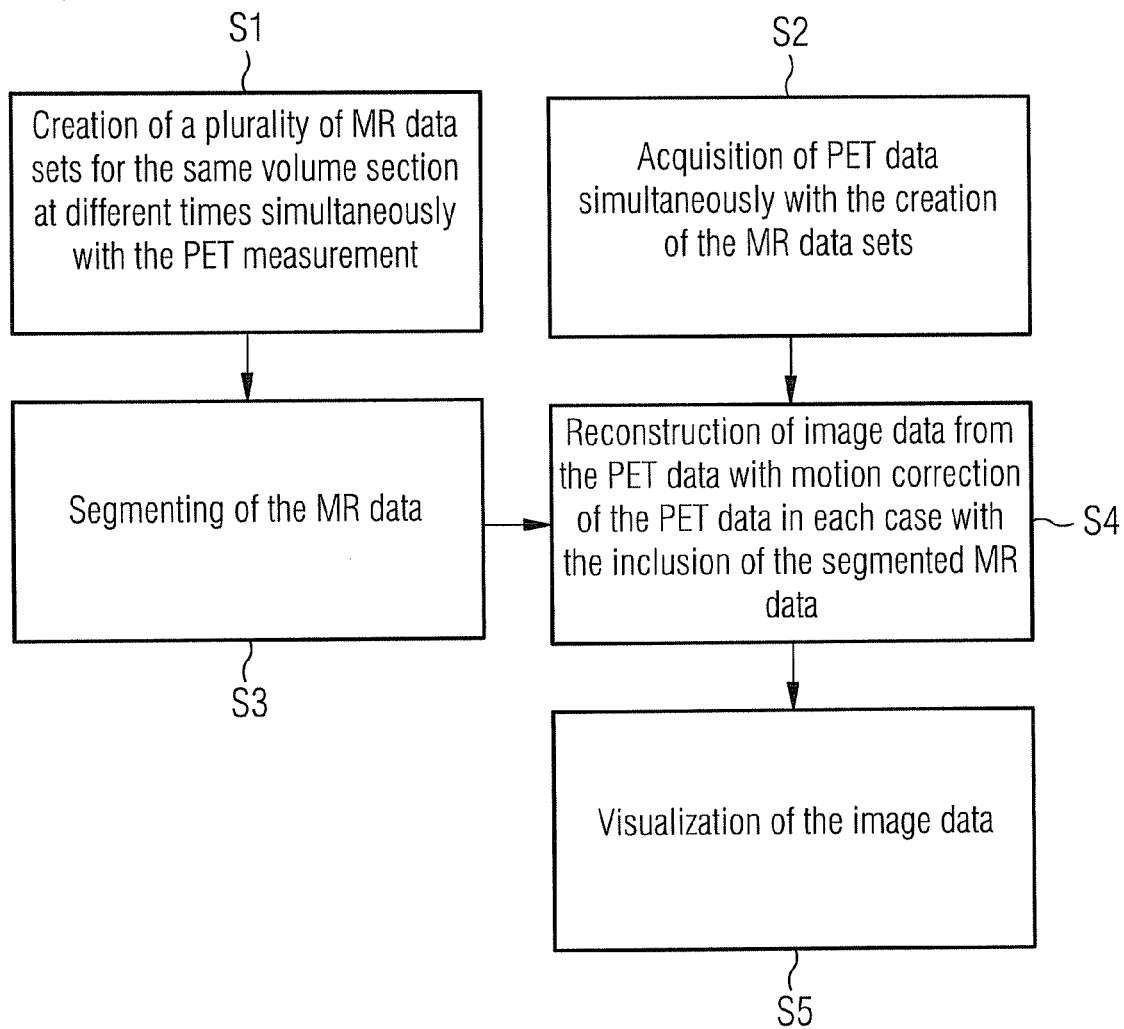

METHOD AND DEVICE FOR IMAGING A VOLUME SECTION BY WAY OF PET DATA

PRIORITY STATEMENT

The present application hereby claims priority under 35 U.S.C. §119 on German patent application number DE 10 2009 017 439.7 filed Apr. 15, 2009, the entire contents of which are hereby incorporated herein by reference.

FIELD

At least one embodiment of the present invention generally relates to a method and/or a device for determining PET data of a volume section by way of PET (Positron Emission Tomography) and magnetic resonance tomography and for using the PET data for imaging the volume section.

BACKGROUND

Positron emission tomography plays an important role these days in oncological diagnostics, for example. In FDG-PET (PET using fluorodeoxyglucose as the radiopharmaceutical) a particular advantage lies in the fact that information about a metabolic status of a lesion can be obtained with the aid of its sugar metabolism. However, a PET examination in the region of the intestine proves to be difficult for the following reasons:

- Different types of tissue can be found in the intestinal region (essentially soft parts, fluid, air, bone) in the field of vision of the PET system, which makes calculating an attenuation correction more difficult. This applies in particular when a combined MR-PET device is used and no computed tomography data can be used for the attenuation correction.
- The volume segment or section to be examined moves due to peristalsis during the examination. Image quality during the PET procedure deteriorates due to the in-motion unsharpness caused thereby and due to a long PET measurement time.
- The intestinal wall is thinner than the resolution to be achieved by the PET system, as a result of which lesions are difficult to detect.

It generally holds true for PET examinations that for any measured event only the line on which a "beta" or positron decay has occurred can be indicated. After being generated a positron also continues to move a short distance, which cannot be reconstructed from the measured values. In PET examinations, for that reason, only a probability distribution can ever be specified for the localization of an event. Added to this are a series of other error sources, such as a false coincidence, for example, which occurs when two photons not originating from the same decay arrive at the detector ring within the coincidence interval.

SUMMARY

In at least one embodiment of the present invention, imaging is improved by way of PET.

In at least one embodiment of the invention, this may be achied by way of a method for imaging a volume section by way of PET data, a device for a combined MR/PET apparatus for imaging a volume section, a combined MR/PET apparatus, a computer program product and/or an electronically readable data medium. The dependent claims define preferred and advantageous embodiment variants of the present invention.

Provided within the scope of at least one embodiment of the present invention is a method for imaging a volume section by way of PET data which are determined by way of a PET. In this case the PET data of the predetermined volume section are acquired with the aid of a positron emission detector. In addition MR data of the predetermined volume section are acquired with the aid of a magnetic resonance system. Using the MR data those PET voxels within all of the voxels within the predetermined volume section are determined from which radiation occurring due to an annihilation which takes place during a PET is emitted. The image data are reconstructed from the PET data by taking into account during the reconstruction that the PET data are generated only by radiation from the PET voxels and not by radiation from other voxels in the predetermined volume section.

With the aid of the MR data (e.g. by segmentation) the predetermined volume section is subdivided into two classes of regions. Beams due to an annihilation are never emitted from the first class of regions, whereas beams of an annihilation can be emitted from the second class of regions. The regions of the first class include the non-PET voxels, whereas the regions of the second class include the PET voxels. In other words a PET voxel is a voxel from which radiation due to an annihilation can potentially be emitted, whereas a non-PET voxel is a voxel from which radiation due to an annihilation is never emitted. When and whether radiation due to an annihilation is in fact emitted at all from a specific PET voxel during the performance of the method according to the invention cannot be predicted with certainty.

Since, however, it is taken into account during the reconstruction of the image data from the PET data that the radiation essential to the generation of the PET data can be emitted only from a specific proportion of the voxels (namely from the PET voxels) within the predetermined volume section, which proportion is determined with the aid of the MR data, the inventive reconstruction of the image data is more accurate than is the case according to the prior art. According to the prior art it is assumed during the reconstruction of image data that the annihilation can occur in any voxel of the predetermined volume section, so it is assumed according to the prior art that the PET data can be generated by way of radiation from any voxel of the predetermined volume section. According to the prior art, therefore, it is not possible to apply any restriction in advance to the PET voxels within the predetermined volume section in order to identify the causative voxel during the recording of PET radiation.

In this case the MR data and the PET data are acquired or recorded in particular essentially simultaneously or in an overlapping manner. This means that the MR data are acquired in a time interval in which the PET data are also acquired. In other words both the MR data and the PET data are acquired in particular by way of a combined MR and PET system which can perform simultaneous MR measurements and PET measurements. A combined MR and PET system of this type is known from US 2007-0102641 A1, the entire contents of which are hereby incorporated herein by reference.

What is to be understood by an essentially simultaneous acquisition of MR data and PET data within the scope of at least one embodiment of the present invention is firstly the simultaneous acquisition of the MR data and the PET data. What is also to be understood by an essentially simultaneous acquisition of the MR data and the PET data is secondly a procedure wherein part of the MR data and part of the PET data is acquired alternately in each case by the same system until all the MR data and PET data of the predetermined volume section have been acquired. In this case a full set of MR data of the predetermined volume section can be acquired multiple times, so that a plurality of MR data sets of the predetermined volume section at different times are available.

In a preferred embodiment variant according to at least one embodiment of the invention a segmentation of the volume section is performed with the aid of the MR data, as a result of which the voxels of the predetermined volume section are classified into two different tissue types or material types. In this case a first tissue type is characterized in that it characterizes tissue in which even after administration of a radiopharmaceutical (a radioactive substance) which is supplied to a patient during a PET, no annihilation and consequently also no radiation occurring due to an annihilation is emitted. A second tissue type is characterized in that it characterizes tissue in which as a result of a radiopharmaceutical being administered an annihilation occurs and consequently corresponding radiation is emitted.

In other words the voxels of the predetermined volume section are distinguished by way of the segmentation, performed with the aid of the MR data, into PET voxels which can emit radiation that is relevant during the PET, and non-PET voxels which cannot emit any radiation that is relevant during the PET.

In particular a uniform distribution of the annihilation events in the PET voxels is assumed for the reconstruction of the image data from the PET data.

Whereas according to the prior art a uniform distribution of the annihilation events in all voxels of the predetermined volume section is therefore generally assumed, the method according to the invention proceeds on the basis of a uniform distribution of the annihilation events only within PET voxels, as a result of which the reconstruction of the image data is more precise than is the case according to the prior art. In other words the uniform distribution relates only to those voxels from which, on the basis of the evaluation of the MR data, radiation due to an annihilation can also be emitted.

In this case an expectation maximization algorithm can be used for the reconstruction of the image data, the expectation maximization algorithm, which is often also referred to as the EM algorithm for short, being an algorithm known from statistical mathematics.

In this case a repetition frequency with which a full MR data set of the predetermined volume section is repetitively acquired is ideally higher than a frequency with which an essentially periodic movement within the predetermined volume section is completed or repeated.

When the predetermined volume section is a section of a human intestine, the repetition frequency should lie above the typical frequency of the peristaltic waves, for example. In this case 3-4 MR data sets of the predetermined volume section are accordingly acquired per minute, the PET measurement ideally taking place continuously over a total measurement time of typically 15-20 min.

According to at least one embodiment of the invention the repetitive MR measurements can be performed at different resolutions. A first or initial MR measurement can be taken for example at a high resolution and for a comparatively longer measurement duration than the following MR measurements, which are performed at a lower resolution and for a shorter measurement duration.

A motion correction of the PET data takes place in the simplest case through the generation of a transformation rule from the acquired MR data, whereby the MR data recorded at different times are registered with one another non-rigidly. This enables parts of the PET data to be reconstructed in such a way that the PET data are deformed with the aid of the obtained transformation rule and computed with one another.

In other words it is determined with the aid of the MR data where a specific voxel has moved to due to a movement (e.g. of the intestine) taking place within the volume section. If a corresponding displacement rule or transformation rule has been determined for each voxel of the predetermined volume section, said transformation rule can also be taken into account during the reconstruction of the image data from the PET data.

The PET data contain too little image information to allow a sufficiently precise transformation rule to be derived therefrom. This disadvantage is removed according to the invention with the aid of the acquired MR data and the transformation rule computed by means of said MR data. In this case the same MR data already acquired for segmentation purposes and therefore for differentiating between the PET voxels and the non-PET voxels can advantageously be used for determining the transformation rule and therefore for motion correction, so no additional measurement time is required for determining the transformation rule and therefore for motion correction.

Furthermore, different data can be determined for the attenuation correction from the MR data for the different time segments during the PET measurement, said data subsequently being taking into account in the reconstruction of the image data from the PET data.

A device for a combined MR/PET apparatus for imaging a predetermined volume section is also provided within the scope of at least one embodiment of the present invention. In this case the device comprises a control unit for controlling both a positron emission detector of the MR/PET apparatus and a magnetic resonance system of the MR/PET apparatus, and an image processing unit which on the one hand accepts PET data of the predetermined volume section acquired by the positron emission detector and on the other hand receives MR data of the predetermined volume section recorded by the magnetic resonance system and reconstructs image data from the PET data. In this case the device is embodied in such a way that with the aid of the MR data the device determines PET voxels within the predetermined volume section from which radiation occurring due to an annihilation is emitted. By means of the image processing unit the device reconstructs the image data from the PET data by taking into account in the process that the PET data are generated only by radiation which is emitted from the PET voxels (and not from other voxels within the predetermined volume section).

The advantages of the device according to embodiments of the invention essentially correspond in this case to the advantages of the method according to embodiments of the invention which have been presented in detail hereintofore, so they will not be repeated at this juncture.

At least one embodiment of the present invention also discloses a magnetic resonance system which includes a device according to at least one embodiment of the invention.

At least one embodiment of the present invention also describes a computer program product, in particular a computer program or piece of software which can be loaded into a memory of a programmable controller or a processing unit of a combined MR/PET apparatus. All or different above-described embodiment variants of the method according to the invention can be performed by way of the computer program product when the computer program product runs in the controller. In this case the computer program product possibly requires program means, e.g. libraries and auxiliary functions in order to implement the corresponding embodiment variants of the methods. In other words the claim directed to the computer program product is intended in particular to place under protection a piece of software by means of which one of the above-described embodiment variants of the method according to at least one embodiment of the invention can be performed. The software can in this case be a source code (e.g. written in C++) which still has to be compiled and linked or which only needs to be interpreted, or an executable software code which only needs to be loaded into the corresponding processing unit in order to execute.

Finally, at least one embodiment of the present invention discloses an electronically readable data medium, e.g. a DVD, a magnetic tape or a USB stick, on which electronically readable control information, in particular software (cf. above), is stored. When said control information (software) is read from the data medium and stored in a controller or processing unit of a combined MR/PET apparatus, all the inventive embodiment variants of the above-described method can be performed.

At least one embodiment of the present invention is suitable in particular for imaging a predetermined volume section in the intestinal region by means of PET data. It goes without saying that at least one embodiment of the present invention is not limited to this preferred field of application, but in principle can be used to improve the image quality for imaging any volume sections outside of the intestinal region.

BRIEF DESCRIPTION OF THE DRAWINGS

The present invention is described in detail below with the aid of example inventive embodiment variants and with reference to the figures, in which:

FIG. 2 is a program flowchart for an embodiment variant of the method according to an embodiment of the invention.

DETAILED DESCRIPTION OF THE EXAMPLE EMBODIMENTS

Figure 1:
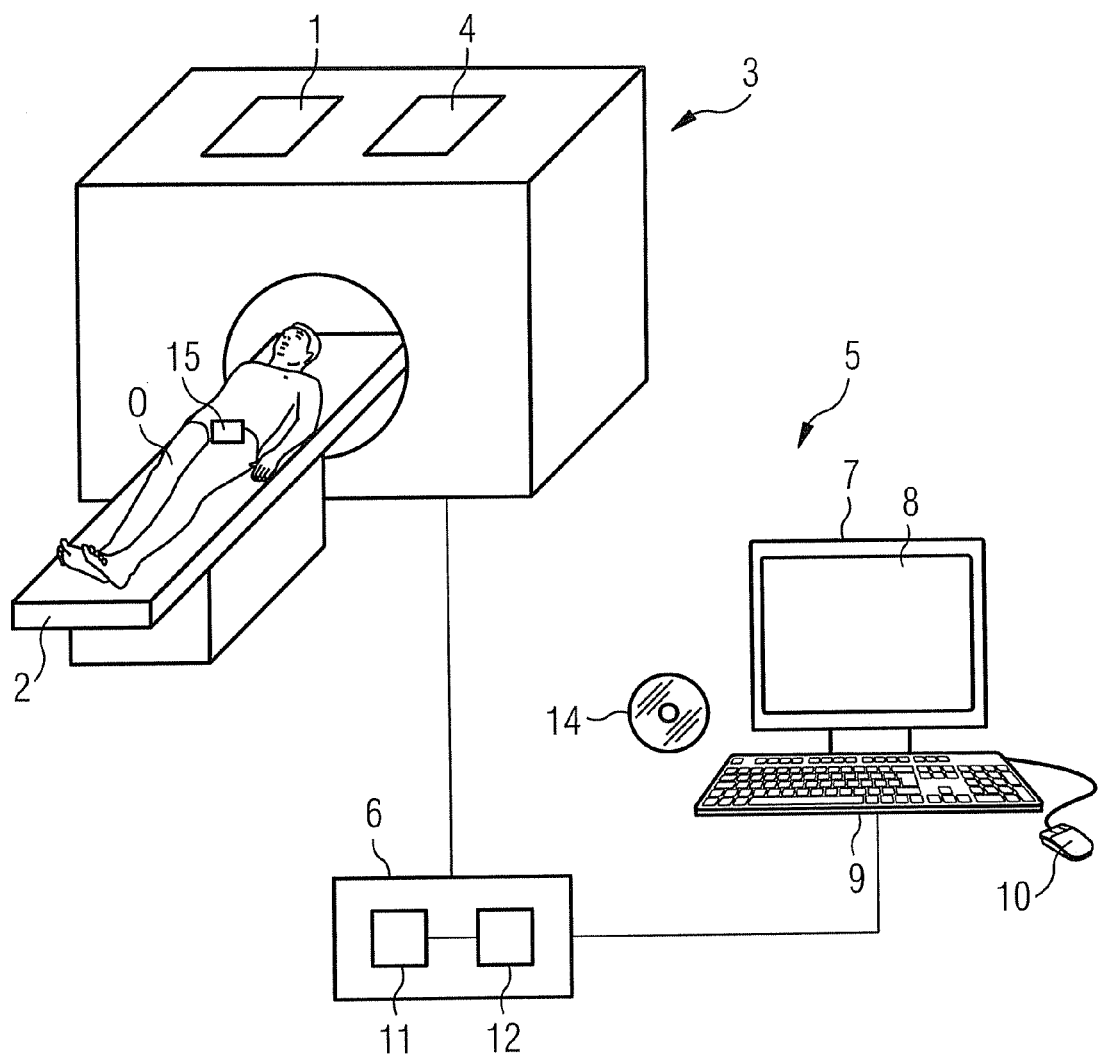
FIG. 1 shows a schematic representation of a combined MR/PET apparatus.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic representation of a combined MR/PET apparatus 5 according to an embodiment of the invention. The combined MR/PET apparatus 5 essentially includes a measurement apparatus 3 for acquiring MR and PET data, a table 2, a device 6 by which the measurement apparatus 3 is controlled, and a terminal 7 connected to the device 6.

The measurement apparatus 3 in turn comprises a positron emission detector 1 by which PET data of a predetermined volume section 15 of a patient O lying on the table 2 are acquired, and a magnetic resonance system 4 by means of which the magnetic field required for the MR measurement is generated and MR data of the predetermined volume section 15 are acquired.

The device 6 for its part includes a control unit 11 and an image processing unit 12. During a PET measurement the PET data and the MR data are acquired by way of the measurement apparatus 3, the measurement apparatus 3 and the table 2 being controlled by the control unit 11.

The image processing unit 12 then edits the PET data with the aid of the MR data in such a way that image data are reconstructed according to an embodiment of the invention and can be graphically displayed on a screen 8 of the terminal 7. In addition to the graphical presentation of the PET data, the terminal 7, which includes a keyboard 9 and a mouse 10 as well as the screen 8, can be used by a user for defining certain parameters, such as e.g. total measurement time, position of the predetermined volume section 15, for the performance of the method according to an embodiment of the invention. The software for the device 6 can also be loaded via the terminal 7, in particular into the image processing unit 12. At the same time this software of the device 6 can also include the method according to the invention. It is also possible here that the method according to an embodiment of the invention is included in software which executes in the terminal 7. Irrespective of which software the method according to an embodiment of the invention is included in, the software can be stored on a DVD 14 so that said software can then be read from the DVD 14 by the terminal 7 and either copied into the device 6 or into a processing unit of the terminal 7 itself.

FIG. 2 shows a program flowchart of an embodiment variant of the method according to an embodiment of the invention.

In this case, in a first method step S1, a plurality of MR data sets for the same volume section 15, which at least partially includes a section of a human intestine, are generated sequentially at different times. At the same time an MR sequence is chosen which allows contrasts (e.g. T2 contrast (contrast based on different T2 times)) which lead to good results in a subsequent segmentation (see method step S3). A plurality of different MR contrasts (contrasts based on different measured values, such as e.g. T1, T2) can be measured during the MR measurements in method step S1.

Simultaneously with method step S1, PET data of the same volume section 15 are acquired in a second method step S2.

During a PET measurement of the intestinal region the peristalsis of the patient O can be inhibited by way of drugs (e.g. Buscopan). This reduces intestinal contractions and hence the movement of the intestinal wall, thereby at least restricting overall a movement of the predetermined volume section that is to be corrected. For the purpose of the combined MR/PET measurement the intestine of the patient O is furthermore filled with a contrast agent which is easy to identify in an MR image. Such a contrast agent can consist e.g. of water to which a bulking agent (e.g. methylcellulose) is possibly added.

In the third method step S3, MR image data are reconstructed by way of the MR data sets and a segmentation into different tissue types is performed with the aid of said MR image data, at least three different types of voxels (air, intestinal contents, tissue) being distinguished. Differentiating between these three types of voxels can in this case be achieved by way of the formation of a simple threshold value, since these three tissue types manifest themselves very differently in an MR measurement (air generates no signal, the intestinal contents generate only a water signal, and the tissue generates a water and a fat signal). During the segmentation, standard contrasts (e.g. a T1 and T2 weighting (division based on the T1 and T2 times)), but also known techniques for fat-water separation, e.g. the Dixon method or a spectral separation, can be used. In this case a water and a fat image can be obtained by way of the Dixon method from the phase relationships between water and fat spins through suitable linear combination of two images recorded at different times by way of a spin-echo sequence (see Dixon WT. Simple Proton Spectroscopic Imaging, Radiology 153:189-194, 1984, the entire contents of which are hereby incorporated herein by reference).

This results in three data sets, a first of these data sets including the voxels of the intestinal contents, a second of these data sets comprising the voxels of the tissue or, as the case may be, of the soft parts, and a third of these data sets including the voxels of the air. Where applicable a further data set comprising the voxels of the bone-like structures or bone can also be segmented so that said data set can be used for the attenuation correction of the PET data. In the simplest case said data sets have only binary information, which means that they only contain information on whether or not the respective voxel is intestinal contents, air, soft part or possibly bone.

If necessary a correction of distortions induced by the magnetic resonance tomography during the MR measurement can be performed in addition.

In the fourth method step S4, image data from the PET data are reconstructed, the MR data acquired in the first method step S1 being used to improve the image definition and for motion correction. The improvement in the image definition is in this case derived from the information that the relevant decay events during the PET must always take place in voxels containing tissue, since neither the intestinal contents nor the air can contain radiotracers (i.e. radioactive material administered to the patient for the purpose of the PET measurement).

According to an embodiment of the invention the information contained in the MR data is taken into account in this case in such a way that, instead of the customary filtered backprojection according to the prior art, an iterative PET reconstruction, using for example an EM algorithm or an algorithm derived therefrom, is performed. In this case, instead of a uniform distribution of the decays over all voxels being assumed as the initial data set for the reconstruction, as is usual according to the prior art, only a uniform distribution over all voxels containing tissue is assumed, since decays cannot occur in any other voxels containing air, intestinal contents or bone.

In addition to the better image quality the approach according to an embodiment of the invention also has the advantage of a shorter reconstruction time, since fewer steps are necessary with the iterative method than is the case according to the prior art. This is based on the realization that the initial data set is already closer to the end result of the iteration, since with said initial data set according to the invention already no decays in the non-PET voxels are taken into account, which according to the prior art is taken into account only partially during the iteration. Because the initial data set is already closer to the end result, the method according to an embodiment of the invention converges more quickly, thus leading to the shorter reconstruction time.

The motion correction of the PET data is in this case carried out in method step S4, with a transformation rule being generated from the MR data. For that purpose the MR data sets of the predetermined volume 15 that were recorded at different times are registered on one another in such a way that a deformation and displacement of the segments is allowed therein, this also being known as non-rigid registration. During the reconstruction of the image data from the PET data the PET data are then deformed on the basis of the generated transformation rule and computed with one another, as a result of which a motion correction of the PET data is carried out and motion artifacts are avoided.

As a result of the non-inclusion of incorrectly registered decays in the reconstruction and as a result of the motion correction, a better image quality with less noise is achieved compared with the prior art. It is particularly advantageous here that the measured MR data simultaneously contribute repetitively to improving the image quality of the image data reconstructed from the PET data, firstly by improving the reconstruction precision, secondly by reducing the in-motion unsharpness, and finally by the attenuation correction.

In the fifth method step S5, finally, the thus reconstructed image data are displayed, wherein the image data reconstructed from the PET data can be presented together with or separately from the image data reconstructed from the MR data.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 Positron emission detector
2 Examination table
3 Measurement apparatus for acquiring MR and PET data
4 Magnetic resonance system
5 Combined MR/PET apparatus
6 Device
7 Computer
8 Screen
9 Keyboard
O Patient
10 Mouse
11 Control unit
12 Image processing unit
14 DVD
15 Volume section
S1-S5 Method step

What is claimed is:

1. A method for imaging a volume section by way of PET data, the method comprising:
  acquiring the PET data of the volume section from a positron emission detector;
  acquiring MR data of the volume section from a magnetic resonance system;
  dividing the volume section into segments based on the acquired MR data, the segments being associated with biological matter of the volume section;
  determining whether to associate the segments with one of PET voxels and non-PET voxels based on whether radiation occurring due to an annihilation is emitted from the segments, wherein segments that emit radiation occurring due to an annihilation are associated with the PET voxels, and segments that do not emit radiation occurring due to an annihilation are associated with the non-PET voxels; and reconstructing PET image data based on only the segments associated with the PET voxels.

2. The method as claimed in claim 1, wherein the PET data and the MR data are acquired essentially simultaneously.

3. The method as claimed in claim 2, wherein the biological matter includes different tissue types.

4. The method as claimed in claim 1, wherein the biological matter includes different tissue types.

5. The method as claimed in claim 1, wherein the reconstructing PET image data includes performing a uniform distribution of the annihilation events in the PET voxels.

6. The method as claimed in claim 1, wherein the reconstructing PET image data is based on an expectation maximization algorithm.

7. The method as claimed in claim 1, wherein the acquiring MR data includes repetitively acquiring the MR data at a repetition frequency higher than a frequency of an essentially periodic movement of at least part of the volume section.

8. The method as claimed in claim 1, wherein the acquiring MR data includes repetitively acquiring the MR data, a first MR measurement of the MR data of the volume section being performed at a higher resolution than MR measurements following the first MR measurement.

9. The method as claimed in claim 1, further comprising:
generating a transformation rule for moving segments of the volume section based on the MR data, the MR data being acquired at different time intervals and registered with one another non-rigidly, wherein the reconstructing the PET image data is based on the transformation rule.

10. The method as claimed in claim 1, further comprising:
acquiring attenuation correction values for the segments based on the MR data, the attenuation correction values being acquired at different time intervals during the acquiring of the MR data and the PET data, wherein the reconstructing PET image data is based on the attenuation correction values.

11. A device for a combined MR/PET apparatus for imaging a volume section, comprising:
a control unit configured to control a positron emission detector of the MR/PET apparatus and a magnetic resonance system of the MR/PET apparatus; and
an image processing unit configured to,
receive PET data of the volume section acquired by the positron emission detector,
receive MR data of the volume section acquired by the magnetic resonance system,
divide the volume section into segments based on the received MR data, the segments being associated with biological matter of the volume section,
determine whether to associate the segments with one of PET voxels and non-PET voxels based on whether radiation occurring due to an annihilation is emitted from the segments, wherein segments that emit radiation occurring due to an annihilation are associated with the PET voxels, and segments that do not emit radiation occurring due to an annihilation are associated with the non-PET voxels, and
reconstruct PET image data based on only the segments associated with the PET voxels.

12. The device as claimed in claim 11, wherein the PET data and the MR data are acquired by the device essentially simultaneously.

13. The device as claimed in claim 12, wherein the biological matter includes different tissue types.

14. The device as claimed in claim 11, wherein the biological matter includes different tissue types.

15. The device as claimed in claim 11, wherein the image processing unit is configured to reconstruct PET image data using a uniform distribution of the annihilation events in the PET voxels.

16. The device as claimed in claim 11, wherein the image processing unit is configured to reconstruct PET image data using an expectation maximization algorithm.

17. The device as claimed in claim 11, wherein the MR data are repetitively acquired for the volume section at a frequency higher than a frequency of an essentially periodic movement of at least part of the volume section.

18. The device as claimed in claim 11, wherein the image processing unit is configured to repetitively acquire the MR data in multiple measurements, a first MR measurement of the MR data of the volume section being at a higher resolution than MR measurements following the first MR measurement.

19. The device as claimed in claim 11, wherein
the image processing unit is configured to generate a transformation rule for moving segments of the volume section based on the MR data, the MR data being acquired at different times and non-rigidly registered with one another, and the image processing unit is configured to reconstruct PET image data based on the transformation rule.

20. The device as claimed in claim 11, wherein
the image processing unit is configured to acquire attenuation correction values for the segments based on the MR data, the attenuation correction values being acquired at different time intervals during a receiving time of the MR data and the PET data, and
the image processing unit is configured to reconstruct PET image data based on the attenuation correction values.

21. A device for a combined MR/PET apparatus for imaging a volume section, comprising:
a control unit configured to control a positron emission detector of the MR/PET apparatus and a magnetic resonance system of the MR/PET apparatus; and
an image processing unit configured to perform the method of claim 1.

22. A combined MR/PET apparatus, comprising:
a magnetic resonance imaging apparatus configured to acquire MR data of a volume section;
a positron emission tomography imaging apparatus configured to acquired PET data of the volume section; and
a device, including,
a control unit configured to control the positron emission apparatus and the magnetic resonance imaging apparatus, and
an image processing unit configured to,
receive PET data of the volume section acquired by the positron emission tomography imaging apparatus,
receive MR data of the volume section acquired by the magnetic resonance imaging apparatus,
divide the volume section into segments based on the received MR data, the segments being associated with biological matter of the volume section,
determine whether to associate the segments with one of PET voxels and non-PET voxels based on whether radiation occurring due to an annihilation is emitted from the segments, wherein segments that emit radiation occurring due to an annihilation are associated with the PET voxels, and segments that do not emit radiation occurring due to an annihilation are associated with the non-PET voxels, and reconstruct PET image data based on only the segments associated with the PET voxels.

23. A computer program product, directly loadable into a memory of a programmable control unit of a combined MR/PET apparatus, comprising program segments for performing all the steps of the method as claimed in claim 1 when the program is executed in the control unit of the combined MR/PET apparatus.

24. A non-transitory electronically readable data medium comprising electronically readable control information stored thereon which is embodied in such a way that when the electronically readable data medium is used in a control unit of a combined MR/PET apparatus, the control information performs the method as claimed in claim 1.

* * * * *